United States Patent [19]

Mori et al.

[11] 4,050,011

[45] Sept. 20, 1977

[54] EDDY CURRENT FLAW DETECTOR USING A PAIR OF PARALLEL RESONANT CIRCUITS AND A NEGATIVE RESISTANCE IN PARALLEL WITH EACH CIRCUIT

[75] Inventors: Toshihiro Mori, Yokohama; Seigo Ando, Kawasaki, both of Japan

[73] Assignee: Nippon Kokan Kabushiki Kaisha, Japan

[21] Appl. No.: 632,116

[22] Filed: Nov. 14, 1975

Related U.S. Application Data

[63] Continuation of Ser. No. 513,083, Oct. 8, 1974, abandoned, which is a continuation of Ser. No. 210,462, Dec. 21, 1971, abandoned.

[51] Int. Cl.² ............................................. G01R 33/12
[52] U.S. Cl. ..................................................... 324/40
[58] Field of Search ..................................... 324/37, 40

[56] References Cited

U.S. PATENT DOCUMENTS

| | | | |
|---|---|---|---|
| 3,252,084 | 5/1966 | Krobath | 324/40 |
| 3,302,105 | 1/1967 | Libby et al. | 324/40 |
| 3,461,400 | 8/1969 | Koda | 324/40 |

Primary Examiner—Robert J. Corcoran
Attorney, Agent, or Firm—William Anthony Drucker

[57] ABSTRACT

When a negative resistance is connected in parallel to a parallel resonance circuit composed of coil and condenser for detecting flaws and other defects of a travelling metal material, the detecting system is capable of improving sensitivity for detecting said flaws and lowering the required degree of amplification of the following amplifier, consequently reducing influence depending upon unbalance of a bridge circuit. At the same time, the simplifying of the power source of said system may be easily realized.

5 Claims, 6 Drawing Figures

INVENTORS
TOSHIHIRO MORI AND SEIGO ANDO
BY
Limton and Limton
ATTORNEYS

EDDY CURRENT FLAW DETECTOR USING A PAIR OF PARALLEL RESONANT CIRCUITS AND A NEGATIVE RESISTANCE IN PARALLEL WITH EACH CIRCUIT

This is a continuation of Ser. No. 513,083 filed Oct. 8, 1974, now abandoned, which is a continuation of Ser. No. 210,462, filed Dec. 21, 1971, now abandoned.

This invention relates to a method and a circuit of testing by eddy current, and more particularly a test by a parallel resonance circuit to which a negative resistance is connected in parallel.

Figure 1:
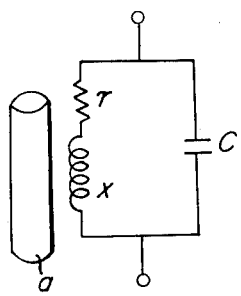

An eddy current flow detecting system is employed to detect flaws and other defects of a travelling metal material, wherein a bridge circuit is included in said detection system. In such case, it is well-known that is reasonable power source is necessary to drive said system and the balancing state of said bridge circuit becomes worse as time passes. Therefore a parallel resonance circuit composed of coil and condenser has been provided as a detecting circuit for said flaws. A typical circuit of such parallel resonance circuit is as shown in FIG. 1, (wherein "a" shows a travelling metal material). In such case, the impedance of the detecting coil is represented as follows:

$$z = r + jx \ldots \quad (1)$$

where, $r$ is resistance component and $x$ is resistance component

It is needless to say that both $r$ and $x$ are a function of applied frequency and a positive number. Now, when a condenser C is in parallel with said detecting coil, its composite admittance is represented as follows:

$$\frac{1}{r + jk} + j\omega C \quad (2)$$

Accordingly, when the following equation is satisfied, said detecting circuit exhibits a parallel resonance.

$$\frac{x}{r^2 + x^2} = \omega C \quad (3)$$

In such parallel resonance circuit, it is impossible to make said $r$ smaller than direct current resistance, and said $x$ becomes smaller as said applied frequency becomes smaller. Consequently, the value of $x/r$ is such that when an applied frequency is low, said circuit tends to be useless.

This invention has been developed to find a way out of said difficulties. The features of this invention lie in that a negative resistance is further parllel-connected to the ordinary parallel resonance detecting coil. Such negative resistance may be realized by a transistor circuit.

An object of this invention is to provide a method of testing, by eddy current such that sensitivity of the applied detecting circuit is heightened to the highest degree. Thereby, the required amplification degree of the following amplifier can be lowered, which remarkably reduces influence of the bridge circuit tending to be unbalanced.

Another object of this invention is to provide a method of testing by eddy current so that simplifying of the power source is realized. In this invention circuit, even if the wave form gets out of shape, there is no influence on the function of detecting circuit, because only voltage is required as a power source of this invention circuit.

Figure 2:
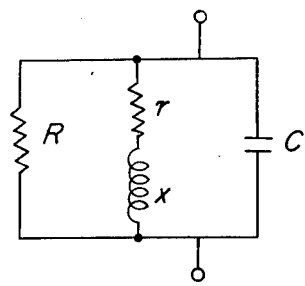
Figure 3:
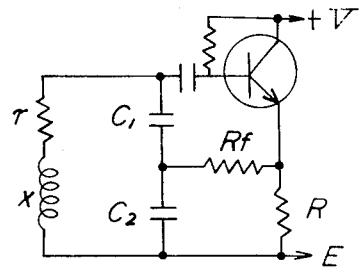
Figure 4:
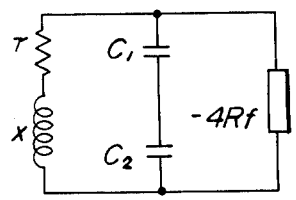
Figure 5:
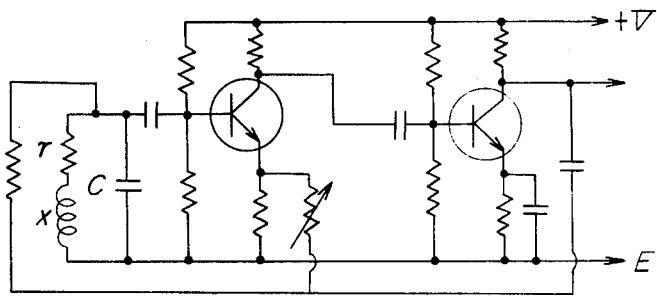
Figure 6:
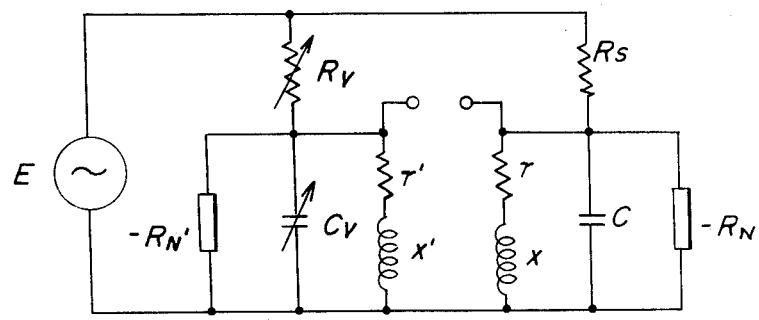

Other objects and advantages will be apparent from the following description and with the accompanying drawing, in which:

FIG. 1 shows a parallel resonance circuit composed of detecting coil and a condenser, FIG. 2 is a basic circuit wherein a resistance is further connected with circuit of FIG. 1, FIG. 3 shows a parallel resonance circuit using a transistor circuit as a negative resistance, FIG. 4 is an equivalent circuit of the circuit of FIG. 3, FIG. 5 adds an oscillator to the circuit of FIG. 3, and FIG. 6 is an example of a bridge circuit based on this invention.

Now, examining the circuit in FIG. 2 wherein a resistance R is further in parallel with the circuit in FIG. 1, its composite admittance will be represented as follows:

$$\frac{1}{H} + \frac{1}{r + jx} + j\omega C \quad (4)$$

And then, the real number field, i.e. conductance, of said admittance is represented as follows:

$$\frac{1}{H} + \frac{r}{r^2 + x^2} \quad (5)$$

If the applied resistance R is a negative resistance, i.e. $-R_N$, it is apparent that the above conductance may be made to get near zero. Speaking in other words, it will be well understood that the more said conductance gets near zero, the more the sensitivity of said detecting circuit is increased. This is the feature of this invention. Such function of negative resistance can be easily realized with a kind of electronic circuit, e.g. transistor, radio tube or the like, FIG. 3 is an example realizing the function of said negative resistance with a transistor circuit. The equivalent circuit is as shown in FIG. 4. That is, the negative resistance $-4R_f$ corresponds to the transistor circuit in FIG. 3.

It is needless to say that there are many modified examples of said transistor circuit acting as a negative resistance. FIG. 5 is another example. In FIG. 5, while a kind of oscillating circuit is applied, its conductance is very low. FIG. 6 is an equivalent circuit of a bridge circuit based on this invention. In FIG. 6, the detecting portions are applied as self-comparative system. Practically, each of negative resistances, i.e. $-R_N$ and $-R_N$, is replaced with a kind of transistor circuit as in FIG. 3, 6 or a similar circuit.

Thus, according to this invention, the heightening of said sensitivity of detecting coil system by well-known eddy current is possible to be obtained with ease. The many advantages thereby, which are mentioned above, has been confirmed as a testing process of practical operation.

What is claimed is:

1. An eddy current flaw detecting apparatus,
   a bridge circuit in which a pair of adjacent arms thereof each include a coil, a condenser and a negative resistance device connected in parallel with each other and forming a resonant circuit, one terminal of said bridge arms being connected in common to one terminal of an energization source, a pair of resistance device connected in common at one end to the other terminal of the source, the other terminal of each resistance device being connected to the other terminal of a respective bridge arm and to a respective output terminal.

2. An eddy current flaw detector according to claim 1, wherein oen of said resistance devices is variable.

3. In the method of detecting flaws in a metal by moving a pair of coils and the metal to be tested relative to each other wherein each of the coils forms a component of a parallel resonant circuit when energized by an oscillator and which provide between them an output signal in response to eddy current variations in said metal, the step of enhancing the sensitivity of said coils to such variations to produce increased output signals which comprises, connecting a negative resistance across each coil to decrease the resistive component of the resonant circuits.

4. In the method according to claim 3 wherein the pair of coils is provided in the opposite like arms of a bridge circuit respectively and wherein an energizing means is connected across a pair of opposite terminals of the bridge and an output signal is derived from the remaining pair of opposite terminals of the bridge to which one end of the coils are respectively connected.

5. In an eddy current flaw detecting system in a metal, a pair of detection coils with respect to which the metal to be tested is moved, each of said coils being located in opposite like arms of a bridge circuit, one end of the coils being connected in common, a negative resistance device connected in parallel with each of said coils, a condenser in parallel with each of said coils and forming therewith and with said negative resistance device a parallel resonant circuit, and a terminal connected to each of the other ends of the coils.

* * * * *